United States Patent [19]

Baldwin

[11] 4,156,004
[45] May 22, 1979

[54] SUBSTITUTED (3-LOWERALKYLAMINO-2-R₁O-PROPOXY)PYRIDINES, AND USE

[75] Inventor: John J. Baldwin, Lansdale, Pa.

[73] Assignee: Merck & Co., Inc., Rahway, N.J.

[21] Appl. No.: 872,962

[22] Filed: Jan. 27, 1978

Related U.S. Application Data

[62] Division of Ser. No. 774,848, Mar. 7, 1977, Pat. No. 4,091,104, which is a division of Ser. No. 696,260, Jun. 15, 1976, abandoned.

[51] Int. Cl.² ............... C07D 213/57; A61K 31/44
[52] U.S. Cl. ................................... 424/263; 546/288
[58] Field of Search ................ 260/294.9; 424/263

[56] References Cited

U.S. PATENT DOCUMENTS

| 4,000,282 | 12/1976 | Baldwin | 260/294.9 |
| 4,060,601 | 11/1977 | Baldwin | 424/263 |

OTHER PUBLICATIONS

Burger, Medicinal Chemistry, Sec. Edition, Interscience Pub., p. 497, RS 403 B.8 C.7 1960.

Primary Examiner—Alan L. Rotman
Attorney, Agent, or Firm—Daniel T. Szura

[57] ABSTRACT

Novel cyano substituted (3-loweralkylamino-2-R₁O-propoxy)pyridines, their pharmaceutically acceptable salts and their preparation are disclosed. The pyridines are vasodilators having antihypertensive activity of rapid onset and extended duration and reduced tendency to cause undesirable tachychardia; they are also β-adrenergic blocking agents.

15 Claims, No Drawings

SUBSTITUTED (3-LOWERALKYLAMINO-2-R₁O-PROPOXY)PYRIDINES, AND USE

This is a division of application Ser. No. 774,848, filed Mar. 7, 1977 now U.S. Pat. No. 4,091,104 which in turn is a division of Ser. No. 696,260, filed June 15, 1976, now abandoned.

BACKGROUND OF THE INVENTION

The present invention concerns cyano substituted 2-(3-loweralkylamino-2-$R_1$O-propoxy)pyridines which have antihypertensive activity of rapid onset and extended duration and are β-adrenergic blocking agents.

Hypertension in man and other animals can be treated with various chemical agents. One such class of agents is that known as the β-adrenergic blocking agents or β-blockers. While this class of agents can have antihypertensive activity, the onset of this activity is generally gradual. The structure and activity of β-blockers is generally discussed in "Clinical Pharmacology and Therapeutics" 10, 252, 306 (1969). Substituted carbocyclic aryl β-adrenergic blocking agents are disclosed in British Pat. No. 1,206,420, British Pat. No. 1,304,303, U.S. Pat. No. 3,644,636, U.S. Pat. No. 3,459,782, Belgian Pat. No. 707,050 and Netherlands Pat. No. 69.0700. Substituted N-heteroaryl β-adrenergic blocking agents are also disclosed in German application No. 2,406,903, its counterpart South African Pat. No. 74.28204, British Pat. No. 1,305,644, Journal of Medicinal Chemistry 16, 1113-1114 (1973) and Journal of Medicinal Chemistry 15, 1321 (1972).

Another class of antihypertensive agents are the vasodilators. Vasodilators, however, normally cause undesirable tachychardia.

Novel cyano substituted (3-loweralkylamino-2-$R_1$O-propoxy)pyridines have been discovered. These compounds have antihypertensive activity of rapid onset and extended duration and they are β-adrenergic blocking agents.

SUMMARY OF THE INVENTION

Novel cyano substituted (3-loweralkylamino-2-$R_1$O-propoxy)pyridines and their pharmaceutically acceptable salts which have rapid and lasting antihypertensive effect and are also β-adrenergic blocking agents.

DESCRIPTION OF THE PREFERRED EMBODIMENTS

An embodiment of the present invention is compounds selected from those having the formula:

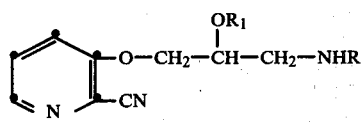

I wherein
R is $C_3$-$C_4$ branched alkyl, and
$R_1$ is selected from H and

L is selected from $C_1$-$C_{10}$ alkyl, phenyl, mono- and disubstituted phenyl wherein said substituents are independently selected from $C_1$-$C_4$ alkyl, C, —$C_4$ alkoxy and halo and pharmaceutically acceptable salts thereof.

The L group includes linear and branched alkyl such as methyl, n-decyl, tert. butyl, isoamyl, n-heptyl and the like with $C_1$-$C_4$ alkyl being preferred; mono and disubstituted phenyl such as 4-tert. butoxyphenyl, 2,6-dibromophenyl, 3-methylphenyl, 4-n-propylphenyl, 3,5-dimethoxyphenyl, 4-iodophenyl, 2-methyl-4-chlorophenyl, p-fluorophenyl and the like: with monosubstituted phenyl preferred. The term halo includes Cl, Br, F and I, with Cl being preferred. R is isopropyl, sec. butyl or tert. butyl, tert. butyl being preferred.

Where $R_1$ is

the more preferred compounds of Formula I are those wherein L is —$CH_3$, —$C(CH_3)_3$ or p-methoxyphenyl, with —$C(CH_3)_3$ being most preferred.

Especially preferred compounds of Formula I are those wherein $R_1$ is hydrogen. The most preferred compounds are those where $R_1$ is hydrogen and R is tert. butyl.

The substituted pyridines of the present invention include all the optical isomer forms, that is mixtures of enantiomers e.g. racemates as well as the individual enantiomers. There individual enantiomers are commonly designated according to the optical rotation they effect, by (+) and (−), (L) and (D), (l) and (d) or combinations of these symbols. The symbols (S) and (R) stand for sinister and rectus respectively and designate an absolute spatial configuration of the enantiomer. Where no isomer designation is given for a compound, the compound is the racemate.

The pyridines of the present invention can be prepared by any convenient process.

One such process involves the coupling of a halopyridine with a suitable substituted oxazolidine and hydrolysing the reaction product obtained. This process is illustrated by the following sets of reaction equations:

REACTION 1

(a)

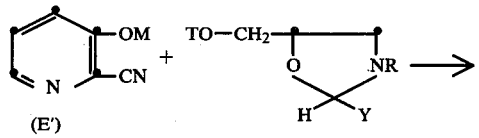

(b)

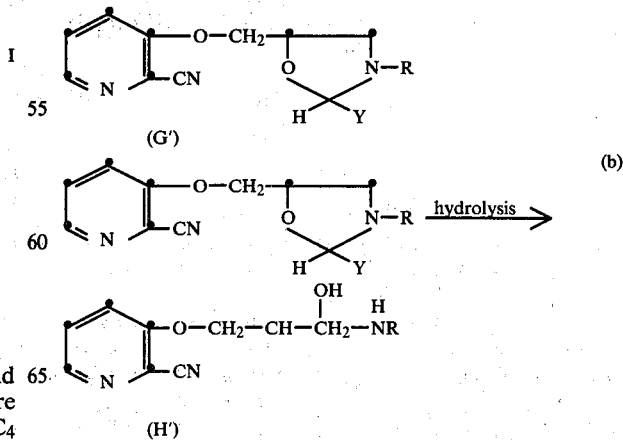

REACTION 2

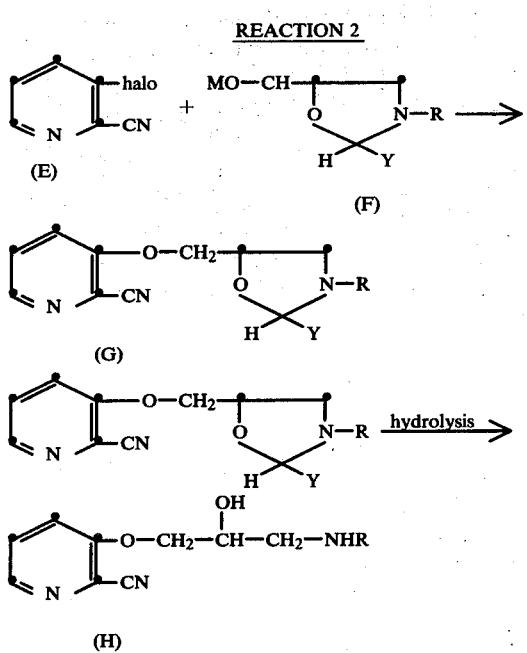

The group T is a conventional aryl or $C_1$–$C_{10}$ alkylsulfonyl group such as methylsulfonyl, decylsulfonyl, butylsulfonyl, benzenesulfonyl, p-bromobenzenesulfonyl, p-methoxybenzenesulfonyl, p-nitrobenzenesulfonyl and the like. Halo may be Cl, I, Br and F, with Cl being preferred. M is an alkali metal, either potassium or sodium. Y can be hydrogen or the residue of any suitable aldehyde

e.g. arylaldehyde, such as benzaldehyde, naphthaldehyde and the like, or alkanal such as acetaldehyde, butyraldehyde and the like. The process for preparing oxazolidines of formula F' having the T-O group and oxazolidines where M is hydrogen is disclosed in U.S. Pat. No. 3,718,647 and U.S. Pat. No. 3,657,237 and to the extent necessary the pertinent disclosure is incorporated herein by reference. The alkali metal salt of the oxazolidine is prepared in a conventional manner by reaction of the corresponding hydroxymethyloxazolidine with an appropriate amount of base reactant. However, Reaction 2 may also be carried out with in-situ formation of the alkali metal oxazolidine salt of Formula F by reacting the oxazolidine

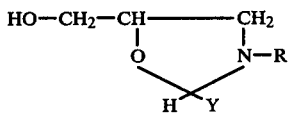

with the Formula E pyridine in the presence of a strong base such as an alkali metal alkoxide (e.g. K—O—C—$(CH_3)_3$) or sodium hydride.

The coupling reaction can be carried out at temperatures ranging from about 0° to about 100° C. A temperature range of about 10° to about 50° C. is preferred. The reaction is generally carried out in a solvent. Any suitable solvent may be used. Examples of useful solvents are dimethylformamide, dimethylsulfoxide, hexamethylphosphoramide, t-butanol and the like. The hydrolysis is carried out using conventional acid hydrolysis reagent and techniques e.g. treatment with a solution of any strong mineral acid such as HCl or $H_2SO_4$. The hydrolysis product can be directly obtained as the salt of the acid used for the hydrolysis. Ordinarily, the product (H) is recovered as the free base after conventional neutralization of the salt.

The coupling reaction is ordinarily carried out at atmospheric pressure. Higher pressures may be used if desired.

When the racemic oxazolidine (Formula F or F' or I') is used as a reactant, the product is obtained as a racemate. The racemate may be separated into its individual enantiomers by conventional resolution techniques.

By using a single optical isomer of solid oxazolidine in the above reactions, the product may be obtained directly as a single enantiomer. Thus, if the S-isomer of the oxazolidine is used, then the product obtained will be the S-isomer. This provides a convenient way for directly preparing individual isomers of the present pyridines.

Pyridines of Formula (I) wherein $R_1$ is other than hydrogen, are conveniently prepared by treating the corresponding pyridine where $R_1$ is hydrogen with an appropriate acylating agent such as an acyl halide, e.g. acetylchloride, pivaloylchloride, p-methoxybenzoylchloride, benzoylchloride, an anhydride e.g. acetic anhydride and the like. The reaction is illustrated by the following equation.

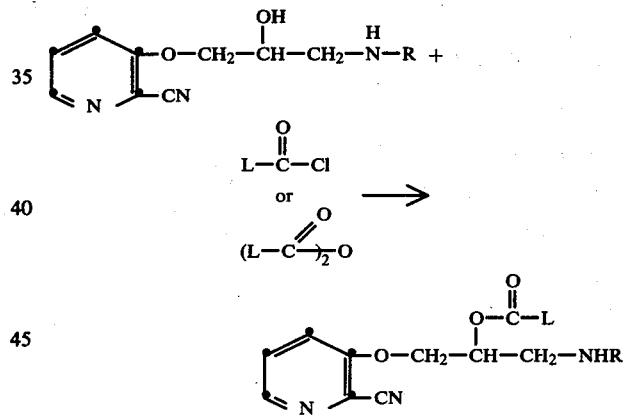

The compounds of the present invention also include the pharmaceutically acceptable salts of the novel pyridines. These salts are generally salts of the Formula I pyridines and organic or inorganic acids. These salts are prepared by treating the pyridine with an appropriate amount of a useful acid, generally in a suitable solvent. Examples of useful organic acids are carboxylic acids such as maleic acid, acetic acid, tartaric acid, propionic acid, fumaric acid, isethionic acid, succinic acid, pamoic acid, oxalic acid, pivalic acid and the like; useful inorganic acids are hydrohalo acids such as HCl, HBr, HI, sulfuric acid, phosphoric acid and the like.

The compounds of the present invention have antihypertensive activity of rapid onset and are also β-adrenergic blocking agents. This antihypertensive activity is believed to be the result of peripheral vasodilation via a mechanism not directly related to β-adrenergic blockade. One advantage the present pyridines have over ordinary β-adrenergic agents is that the antihypertensive effect is immediate and generally of extended duration.

This rapid onset, antihypertensive activity is determined by administering a representative pyridine of the present invention to spontaneously hypertensive (SH) rats and measuring the effect on blood pressure. An example of a representative compound having this antihypertensive activity is (S)-3-(3-tert. butylamino-2-hydroxypropoxy) 2-cyanopyridine.

The β-adrenergic blocking activity of the present pyridines is determined by measuring the ability of a representative pyridine to block isoproterenol induced β-adrenergic stimulant effects such as heart rate increase, hypotension and bronchodilatation, in animals.

The ability of the present pyridines to reduce blood pressure, in an SH rat, rapidly and for extended duration, indicates that the present pyridines and their salts are useful to treat hypertension in humans. Likewise, the observed β-adrenergic blocking activity of these pyridines indicates that they are useful in humans as β-adrenergic blocking agents.

For use as antihypertensives and/or β-adrenergic blocking agents, the compounds of the present invention can be administered orally, by inhalation, by suppository or parenterally i.e. intravenously, intraperitoneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material; or (2) for parenteral administration, dissolved, dispersed, or emulsified in a suitable liquid carrier or diluent or (3) as an aerosol or (4) as a suppository. The ratio of active ingredient (present pyridine) to compounding ingredients will vary as the dosage form required. Conventional procedures are used to prepare the pharmaceutical formulations.

The dosage level for the present compounds may be varied from about 0.01 mg. to about 50 mg. per kilogram of animal body weight per day. Daily doses ranging from about 0.04 to about 2.5 mg/kg are preferred, with about 0.08 to about 1.25 mg/kg being a more preferred range. Oral administration is preferred. Either single or multiple daily doses may be administered depending on unit dosage.

Thus, another embodiment of this invention is a pharmaceutical composition containing an antihypertensive and/or β-adrenergic blocking amount of a compound of the present invention.

The following examples illustrate the preparation of representative pyridines of the present invention. Where no isomer designation is indicated, the product is the racemate. All parts are by weight unless otherwise noted.

EXAMPLE 1

S-2-Cyano-3-(3-tert. butylamino-2-hydroxypropoxy)-pyridine hydrogen maleate

A solution of S-2-phenyl-3-tert. butyl-5-hydroxymethyloxazolidine (5.8 g., 0.024 m) in pyridine (8ml.) is cooled to 0°–4° C. and treated portionwise with p-toluenesulfonyl chloride (4.7 g., 0.025 m). The cooled solution is slowly warmed to room temperature while not allowing the temperature of the mixture to exceed 30° C. After 3 hours, the semi-solid mixture is treated with a solution of $K_2CO_3$ (3.4 g.) in $H_2O$ (50 ml.) and extracted with $CHCl_3$ (3×100 ml.), dried over $Na_2SO_4$, filtered and concentrated to dryness under reduced pressure (30 mm) and finally at 60° C. and 1 mm. The residue oil is dissolved in NN-dimethylformamide (25 ml.) and added dropwise to a solution of 3-hydroxy-2-cyanopyridine (2.6 g., 0.0217 m), 57% NaH 91.1 g., 0.023 m) and NN-dimethylformamide (50 ml.) at room temperature under $N_2$ with stirring. The solution is heated to reflux for 18 hours, and then concentrated to dryness under reduced pressure (1 mm). The residue is treated with saturated $Na_2CO_3$ solution (200 ml.), extracted with ethyl acetate (200 ml.), then $CH_2Cl_2$ (2×200 ml.). The extract is then dried over $Na_2SO_4$, filtered and concentrated to dryness under reduced pressure (30 mm.). The residual oil is treated with 1N HCl (90 ml.), heated on a steam bath for 15 minutes, cooled to room temperature, and extracted with ether (2×100 ml.). The aqueous layer is neutralized with saturated $Na_2CO_3$ solution (100 ml) and extracted with $CHCl_3$ (3×100 ml.), dried over $Na_2SO_4$, filtered and concentrated to dryness under reduced pressure (30 mm). The residue is chromatographed on silica gel and the product eluted with 50% $MeOH-CHCl_3$. After concentration of the solvent, the residual oil is crystalized as the hydrogen maleate salt, from isopropanol. The yield of S-2-cyano-3-(3-tert. butylamino-2-hydroxypropoxy)pyridine (M.P.=168°–170° C.) was 1.9 grams.

Isopropyl or sec. butyl amino analogues of the compound of the above example are prepared by substituting suitable oxazolidines e.g. 2-phenyl-3-isopropyl-5-hydroxymethyloxazolidine, (S)-2-methyl-3-sec. butyl-5-hydroxymethyloxazolidine, 3-isopropyl-4-hydroxymethyloxazolidine for the (S)-2-phenyl-3-tert. butyl-5-hydroxymethyloxazolidine reactant.

Pyridines of Formula I where $R_1$ is

are prepared by treating the corresponding pyridines where $R_1$ is —OH with a suitable acylating agent. For example, the pyridine having the formula

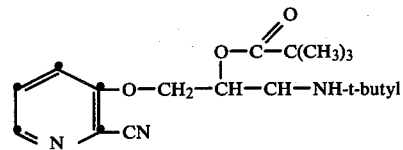

is prepared by treating the Example I product (or the free base) with an appropriate amount of pivaloylchloride (trimethylacetylchloride).

The present invention also includes the quaternary ammonium salts and N-pyridine oxides of the Formula I compounds.

The quaternary ammonium salts have the formula

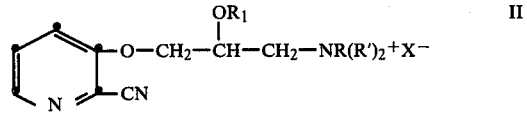

II wherein R and $R_1$ are as defined above, R' is an alkyl (e.g. $C_1-C_4$ alkyl) or aryl (e.g. benzyl) group and X is a halogen, especially Cl, Br or I. These quaternary salts are prepared using any convenient method. For example, they can be prepared by treating the compound of Formula I with an alkyl or aryl halide such as methyliodide or benzylchloride to obtain the corresponding quaternary salt of Formula II.

The N-pyridine oxides have the formula $$\text{III}$$

wherein R and $R_1$ are as defined above, including the acid addition salts and quaternary ammonium salts thereof. These N-oxides are also prepared using conventional reagents and procedures. For example, a convenient method of preparing these oxides is to treat the intermediate of Formula E or E' with an oxidizing agent e.g. $H_2O_2$ using conventional reaction conditions to produce the oxidized intermediate having the formula

E-1    E-2

The formula E1 or E2 compound is then substituted for the Formula E or E' compound, respectively, in Reaction 1 or 2 above to obtain the N-pyridine oxide of Formula III.

Claims to the invention follow.

What is claimed is:

1. Compound having the formula:

$$\text{or}$$

wherein

R is $C_3-C_4$ branched alkyl
$R_1$ is selected from H and $$-\overset{O}{\underset{\|}{C}}-L$$

wherein L is selected from $C_1-C_{10}$ alkyl, phenyl, mono- and disubstituted phenyl wherein said substituents are independently selected from $C_1-C_4$ alkyl, $C_1-C_4$ alkoxy and halo, R' is $C_1-C_4$ alkyl or benzyl and X is halogen.

2. The compound of claim 1 having the S-isomer configuration.

3. The compound of claim 1 wherein R is tert.-butyl.

4. The compound of claim 1 wherein $R_1$ is $$-\overset{O}{\underset{\|}{C}}-L.$$

5. The compound of claim 4 wherein L is selected from $C_1-C_4$ alkyl, phenyl and monosubstituted phenyl.

6. The compound of claim 4 wherein $R_1$ is selected from $$-\overset{O}{\underset{\|}{C}}-C(CH_3)_3, \quad -\overset{O}{\underset{\|}{C}}-CH_3$$

and p-methoxybenzoyl.

7. The compound of claim 6 wherein R is tert butyl.

8. The compound of claim 1 wherein $R_1$ is hydrogen.

9. The compound of claim 8 having the S-isomer configuration.

10. The compound of claim 8 wherein R is tert. butyl.

11. The compound of claim 10 having the S-configuration.

12. A pharmaceutical composition for treating hypertension comprising an antihypertensive effective amount of compound of claim 1 and a diluent or carrier.

13. A method of treating hypertension in hypertensive animals which comprises administering an effective amount of a compound of claim 1.

14. Compound of claim 1 having the formula

15. Compound of claim 1 having the formula

* * * * *